United States Patent
Kim et al.

(10) Patent No.: US 10,913,032 B2
(45) Date of Patent: Feb. 9, 2021

(54) 3D POLYMER NANOFIBER MEMBRANE COMPOSED OF 1D INDIVIDUAL POLYMER NANOFIBERS WHICH ARE QUASI-ALIGNED AND CROSS-LAMINATED LIKE GRID STRUCTURE WITH FUNCTIONS OF CONTROLLING PORE DISTRIBUTION AND SIZE, AND MANUFACTURING METHOD THEREOF

(71) Applicant: Korea Advanced Institute of Science and Technology, Daejeon (KR)

(72) Inventors: Il-Doo Kim, Daejeon (KR); Chanhoon Kim, Daejeon (KR); Su Ho Cho, Daejeon (KR); Won Tae Hwang, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 518 days.

(21) Appl. No.: 15/648,807

(22) Filed: Jul. 13, 2017

(65) Prior Publication Data

US 2018/0015423 A1    Jan. 18, 2018

(30) Foreign Application Priority Data

Jul. 15, 2016    (KR) ........................ 10-2016-0089649

(51) Int. Cl.
*B01D 53/22*    (2006.01)
*B01D 67/00*    (2006.01)
(Continued)

(52) U.S. Cl.
CPC ......... *B01D 67/0002* (2013.01); *B01D 71/26* (2013.01); *B01D 71/58* (2013.01);
(Continued)

(58) Field of Classification Search
CPC .... B01D 67/0002; B01D 71/26; B01D 71/58; B01D 2323/39; C12M 25/02;
(Continued)

(56) References Cited

U.S. PATENT DOCUMENTS

2007/0269481 A1* 11/2007 Li .......................... A61L 27/18
424/423
2008/0110342 A1* 5/2008 Ensor ................. D01D 5/0076
96/54

(Continued)

FOREIGN PATENT DOCUMENTS

KR    10-2014-0050874    4/2014
KR    10-1506403    3/2015

OTHER PUBLICATIONS

Machine Translation YU KR 10-2014-0050874 Feb. 9, 2017, 14 pages (Year: 2017).*

*Primary Examiner* — Anthony R Shumate
(74) *Attorney, Agent, or Firm* — Hamilton, Brook, Smith & Reynolds, P.C.

(57) ABSTRACT

Disclosed is a 1D nanofibers quasi-aligned, grid structure cross-laminated, and pore distribution and size controlled 3D polymer nanofiber membrane, and manufacturing method thereof. A 3D polymer nanofiber membrane controlled in pore size and porosity is formed by employing an electrospinning pattern forming apparatus that includes double insulating blocks quasi-aligns nanofibers in a specific direction by transforming an electric field and includes a current collector rotatable in 90°. Additionally, the 3D polymer nanofiber membrane may be used for air filters, separator, water filters, cell culture membranes, and so on by allowing various properties thereto through a functional surface coating.

22 Claims, 13 Drawing Sheets

100: 3D POLYMER NANOFIBERS MEMBRANE
110: 1D INDIVIDUAL POLYMER NANOFIBER

(51) Int. Cl.
*D01D 5/00* (2006.01)
*B01D 71/26* (2006.01)
*B01D 71/58* (2006.01)
*C12M 1/12* (2006.01)
*C12M 1/26* (2006.01)
*D01F 6/18* (2006.01)
*D01F 6/66* (2006.01)

(52) U.S. Cl.
CPC ............. *C12M 25/02* (2013.01); *D01D 5/003* (2013.01); *D01D 5/0038* (2013.01); *D01D 5/0069* (2013.01); *D01D 5/0076* (2013.01); *D01D 5/0092* (2013.01); *B01D 2323/39* (2013.01); *C12M 33/14* (2013.01); *D01F 6/18* (2013.01); *D01F 6/66* (2013.01); *D10B 2505/04* (2013.01)

(58) Field of Classification Search
CPC ..... C12M 33/14; D01D 5/003; D01D 5/0038; D01D 5/0069; D01D 5/0076; D01D 5/0092; D01F 6/18; D01F 6/66; D10B 2505/04

See application file for complete search history.

(56) References Cited

U.S. PATENT DOCUMENTS

| | | | |
|---|---|---|---|
| 2012/0295021 A1* | 11/2012 | Peno | D01D 5/0076 427/180 |
| 2013/0312638 A1* | 11/2013 | Parker | A61B 17/12168 106/156.2 |
| 2015/0202423 A1* | 7/2015 | Adenusi | A61L 29/085 428/36.4 |
| 2016/0289865 A1* | 10/2016 | Park | D01D 5/0023 |
| 2018/0097216 A1* | 4/2018 | Joo | H01M 10/4235 |
| 2018/0161185 A1* | 6/2018 | Kresslein | D01D 5/003 |
| 2019/0314746 A1* | 10/2019 | Leung | B32B 5/26 |
| 2020/0058957 A1* | 2/2020 | Kwon | H01M 10/0525 |

* cited by examiner

100: 3D POLYMER NANOFIBERS MEMBRANE
110: 1D INDIVIDUAL POLYMER NANOFIBER

200: GRID STRUCTURE QUASI-ALIGNED 3D POLYMER NANOFIBER MEMBRANE
210: 1D INDIVIDUAL POLYMER NANOFIBER

3D POLYMER NANOFIBER MEMBRANE COMPOSED OF 1D INDIVIDUAL POLYMER NANOFIBERS WHICH ARE QUASI-ALIGNED AND CROSS-LAMINATED LIKE GRID STRUCTURE WITH FUNCTIONS OF CONTROLLING PORE DISTRIBUTION AND SIZE, AND MANUFACTURING METHOD THEREOF

RELATED APPLICATION(S)

A claim for priority under 35 U.S.C. § 119 is made to Korean Patent Application No. 10-2016-0089649 filed Jul. 15, 2016, in the Korean Intellectual Property Office, the entire contents of which are hereby incorporated by reference.

BACKGROUND

Embodiments of the inventive concept described herein relate to a 3D polymer nanofiber membrane composed of 1D individual polymer nanofibers which are quasi-aligned and cross-laminated like grid structure with functions of controlling pore distribution and size and a manufacturing method thereof, and more particularly, relate to a 3D polymer nanofiber membrane composed of 1D individual polymer nanofibers which are quasi-aligned and cross-laminated like grid structure with functions of controlling pore distribution and size and a manufacturing method thereof.

Membranes for filtering or separating have been playing important roles for the past several decades in the high technology sectors, such as automobiles, aerospace, and new materials, as well as the traditional sectors including chemistry, food, and medicine. The fiber membrane industry has been globally recording sustained double digit growth or more in non-clothing fiber industry and in recent years, the filter market in the environmental industry is expected to rapidly grow under the increasing influence from the hazard of microdusts.

With a recent increase in employing nanofibers for membranes, there are actively advancing many studies and developments for manufacturing nanofibers through electrospinning processes. The electrospinning is a method to produce nanofibers when an electrostatic force is applied to a melted material or polymer solution having viscosity, from the discovery by Bose in 1795 for an electrostatic spray phenomenon that discharges microscopic filaments from the surface of a waterdrop, which forms at the end of a capillary tube due to surface tension, in response to a high voltage. The electrospinning technology which has several merits such as capital-intensiveness, lower early investment costs for facilities, and more economical system in manufacturing nanofibers of mass production than the traditional fiber production systems for mass production, has been widely applied to the sectors over fibers, chemistry, materials, and life science. The electrospinning may be used for manufacturing for polymer fibers ranged from several tens nanometers to several micrometers with high efficiency, high uniformity and, high aspect ratios. For example, it is possible for producing a uniform nanofiber in the length of 130,000 km and the diameter of 100 nm from polyethylene of 1 g. Additionally, it is permissible to electrospin with a mixture with two or more kinds of polymers and even to make core-shell structured nanofibers in a case, thus capable of producing nanofibers with different polymer characteristics. In recent years, there are some reports about successful commercial cases that nanofibers obtained through the electrospinning are employed as primary materials of secondary battery separators, chemical and bio sensors, and high-performance filters. Despite the successful commercialization, a nanofiber mat manufactured through the present electrospinning process still has a random distribution of nanofibers with pores with very different sizes. This is because nanofibers are randomly arranged on the top of a current collector while a charged polymer solution is jetting out of a Taylor cone beyond surface tension when an electric field higher than specific strength applied to the polymer solution in the condition that the polymer solution formed at the end of a capillary tube appears in a hemisphere drop on equilibrium between gravity and surface tension. Controlling a distribution and sizes of pores is very important in industry and necessary by all means especially for microfiltration membranes and filters. Therefore, it needs to develop a new process that has the merits of the electrospinning capable of very efficiently producing nanofibers in a large quantity and accomplishes technically compositive development capable of controlling a distribution and sizes of pores.

SUMMARY

Embodiments of the inventive concept, relating to a 1D polymer nanofibers quasi-aligned and grid structure cross-laminated 3D polymer nanofiber membrane and a manufacturing method thereof, provide a 1D polymer nanofibers grid structure cross-laminated, and pore distribution and size controlled 3D polymer nanofiber membrane and a manufacturing method thereof through a simple and large-scale productive process.

According to an aspect of the inventive concept, a 3D polymer nanofiber membrane composed of crossed or paralleled 1D polymer nanofibers, which are laminated, includes a quasi-aligned 3 D network structure with thickness of several micrometers.

In the 3D polymer nanofiber membrane composed of 1D individual polymer nanofibers which are quasi-aligned and cross-laminated like grid structure, a polymer composed of the 1D polymer nanofibers is one or a mixture with two or more among polyurethane, polyurethane copolymer, cellulose acetate, cellulose, acetate butylate, cellulose derivative, styrene-acrylonitrile (SAN), polyacrylonitrile (PAN), poly (vinyl acetate) (PVAc), polyvinylpyrrolidone (PVP), polyvinyl alcohol (PVA), polyethylene oxide (PEO), polyacrylic acid (PAA), hydroxypropyl cellulose (HPC), polymethylmethacrylate (PMMA), polyfurfuryl alcohol (PFA), polystyrene (PS), polystyrene copolymer, polyaniline (PANT), polyvinylchloride (PVC), poly(vinylidene fluoride) (PVDF), polyethylene terephthalate (PET), polypropylene (PP) or polyethylene (PE), and polyimide.

It should be understood that 1D individual nanofibers of the 3D polymer nanofiber membrane composed of 1D individual polymer nanofibers which are quasi-aligned and cross-laminated like grid structure with functions of controlling pore distribution and size may have diameters ranged from 50 nm to 2 µm. It may be more preferred to select diameters of the 1D individual nanofibers in the range from 100 nm to 500 nm. In the case that diameters of the 1D individual nanofibers are smaller than 100 nm, a separation effect may be degraded due to an excessive increase of the porosity of the nanofiber membrane. In the case that diameters of the 1D individual nanofibers are higher than 500 nm, a separation effect may be also degraded due to a remarkable decrease of the porosity of the nanofiber membrane.

The 3D polymer nanofiber membrane composed of 1D individual polymer nanofibers which are quasi-aligned and cross-laminated like grid structure with functions of controlling pore distribution and size may include pores having an average diameter ranged from 10 nm to 10 µm. It may be more preferred for the 3D polymer nanofiber membrane to include pores having an average diameter of 50 nm to 1 µm. In the case that diameters of the pores are smaller than 50 nm, the separation efficiency may be degraded due to a remarkable decrease of the porosity of the nanofiber membrane. In the case that diameters of the pores are equal to or larger than 1 µm, the separation efficiency may be also degraded due to an excessive increase of porosity.

The 3D polymer nanofiber membrane composed of 1D individual polymer nanofibers which are quasi-aligned and cross-laminated like grid structure with functions of controlling pore distribution and size may have a thickness ranged from 5 to 200 µm. It may be more preferred to select a thickness of the 3D polymer nanofiber membrane from the range from 20 to 100 µm. In the case that a thickness of the 3D polymer nanofiber membrane is smaller than 20 µm, it would be concerned of degradation in mechanical strength. In the case that a thickness of the 3D polymer nanofiber membrane is larger than 100 µm, a degree of alignment of the nanofibers may be abruptly lower to cause regular pore distribution control to be difficult.

The 3D polymer nanofiber membrane composed of 1D individual polymer nanofibers which are quasi-aligned and cross-laminated like grid structure with functions of controlling pore distribution and size may have nanofibers at least equal to or more than 80% which are distributed in parallel with each other.

The 3D polymer nanofiber membrane composed of 1D individual polymer nanofibers which are quasi-aligned and cross-laminated like grid structure with functions of controlling pore distribution and size may have an area ranged from 1 cm² to 1 m².

An electrospinning pattern forming apparatus capable of manufacturing the 3D polymer nanofiber membrane composed of 1D individual polymer nanofibers which are quasi-aligned and cross-laminated like grid structure with functions of controlling pore distribution and size may include a high voltage generator, a rotatable conductive current collector, and a polymer solution injection nozzle connected to a metering pump, and double insulating blocks. With this configuration, the conductive current collector may be placed on a conductive substrate which is grounded. The grounded conductive substrate may be used as a cathode while the injection nozzle attached to the metering pump controlled in a discharge amount per time may be used as an anode. The high voltage generator may be selected in a range from 1 to 30 kV. It may be preferred to adjust and apply a voltage from 5 to 20 kV. Then, the 3D polymer nanofiber membrane composed of 1D individual polymer nanofibers which are quasi-aligned and cross-laminated like grid structure with functions of controlling pore distribution and size may be manufactured by regulating a solution discharge rate in 5 to 200 µl/minute.

The double insulating blocks may arrange the nanofibers by transforming an electric field and applying the transformed electric field to the nanofibers in a specific direction.

The double insulating blocks may be formed of a material which has a relative permittivity equal to or lower than 50. For example, the double insulating blocks may be made of one or more materials selected from a group of a Styrofoam material, a Teflon material, a wooden material, a plastic material, a glass material, a quartz material, a silicon oxide material, and a metallic material.

A grid structured 3D membrane may be formed through repeated lamination of the nanofibers after rotating the rotatable conductive current collector by 90° after laminating one layer of the nanofibers.

The double insulating blocks of the electrospinning pattern forming apparatus may have widths and lengths ranged from 3 to 8 cm and heights ranged from 2 to 5 cm, and the two parallel insulating blocks may have an interval ranged from 1 to 6 cm. An interval between top surfaces of the double insulating blocks and a tip of the nozzle may be ranged from 2 to 5 cm. An interval between bottom surfaces of the double insulating blocks and the conductive current collector may be ranged in 2 to 5 cm.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
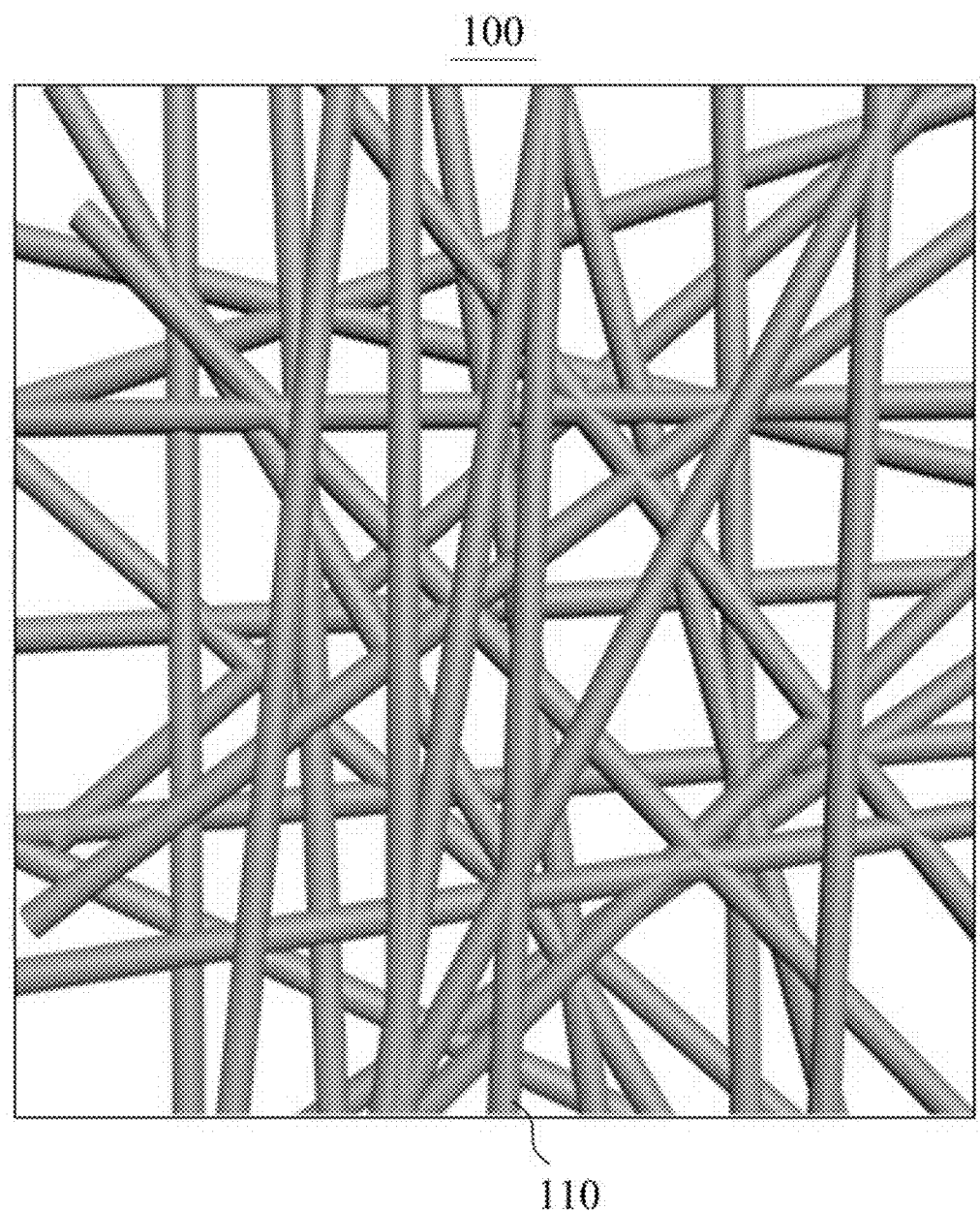
FIG. 1 is a schematic diagram illustrating a 3D polymer nanofiber membrane manufactured through a general electrospinning method according to a comparison example.

Hereinafter, embodiments of the inventive concept will be described below about a method of manufacturing the 3D polymer nanofiber membrane composed of 1D individual polymer nanofibers which are quasi-aligned and cross-laminated like grid structure with functions of controlling pore distribution and size in conjunction with the accompanying figures.

In embodiments of the inventive concept, it should be understand that a polymer forming the 3D polymer nanofiber membrane composed of 1D individual polymer nanofibers which are quasi-aligned and cross-laminated like grid structure with functions of controlling pore distribution and size may be one, or one or more selected from a group of compositions with polyurethane, polyurethane copolymer, cellulose acetate, cellulose, acetate butyrate, cellulose derivative, styrene-acrylonitrile (SAN), polyacrylonitrile (PAN), poly(vinyl acetate) (PVAc), polyvinylpyrrolidone (PVP), polyvinyl alcohol (PVA), polyethylene oxide (PEO), polyacrylic acid (PAA), hydroxypropyl cellulose (HPC), polymethylmethacrylate (PMMA), polyfurfuryl alcohol (PFA), polystyrene (PS), polystyrene copolymer, polyaniline (PANT), polyvinylchloride (PVC), poly(vinylidene fluoride) (PVDF), polyethylene terephthalate (PET), polypropylene (PP) or polyethylene (PE), and polyimide.

In embodiments of the inventive concept, it should be understood that 1D individual nanofibers of the 3D polymer nanofiber membrane composed of 1D individual polymer nanofibers which are quasi-aligned and cross-laminated like grid structure with functions of controlling pore distribution and size may have diameters ranged from 50 nm to 2 μm. It may be more preferred to select diameters of the 1D individual nanofibers in the range from 100 nm to 500 nm. In the case that diameters of the 1D individual nanofibers are smaller than 100 nm, a separation effect may be degraded due to an excessive increase of the porosity of the nanofiber membrane. In the case that diameters of the 1D individual nanofibers are higher than 500 nm, a separation effect may be also degraded due to a remarkable decrease of the porosity of the nanofiber membrane.

In embodiments of the inventive concept, the 3D polymer nanofiber membrane composed of 1D individual polymer nanofibers which are quasi-aligned and cross-laminated like grid structure with functions of controlling pore distribution and size may have a thickness ranged from 5 to 200 μm. It may be more preferred to select a thickness of the 3D polymer nanofiber membrane from the range from 20 to 100 μm. In the case that a thickness of the 3D polymer nanofiber membrane is smaller than 20 μm, it would be concerned of degradation in mechanical strength. In the case that a thickness of the 3D polymer nanofiber membrane is larger than 100 μm, a degree of alignment of the nanofibers may be abruptly lower.

In embodiments of the inventive concept, the 3D polymer nanofiber membrane composed of 1D individual polymer nanofibers which are quasi-aligned and cross-laminated like grid structure with functions of controlling pore distribution and size may have nanofibers with their members at least equal to or more than 80% that are parallel or aligned in angles, which are equal to or smaller than 10°, to their adjacent polymer nanofibers.

In embodiments of the inventive concept, the 3D polymer nanofiber membrane composed of 1D individual polymer nanofibers which are quasi-aligned and cross-laminated like grid structure with functions of controlling pore distribution and size may include pores having an average diameter ranged from 10 nm to 10 μm. It may be more preferred for the 3D polymer nanofiber membrane to include pores having an average diameter of 50 nm to 1 μm. In the case that diameters of the pores are smaller than 50 nm, the separation efficiency may be degraded due to a remarkable decrease of the porosity of the nanofiber membrane. In the case that diameters of the pores are equal to or larger than 1 μm, the separation efficiency may be also degraded due to an excessive increase of porosity.

In embodiments of the inventive concept, the 3D polymer nanofiber membrane composed of 1D individual polymer nanofibers which are quasi-aligned and cross-laminated like grid structure with functions of controlling pore distribution and size may have porosity ranged from 50 to 90%. In the case that porosity is equal to or higher than 90%, such excessive porosity may degrade a separation effect. In the case that porosity is equal to or lower than 50%, transmittance thereof may be degraded.

In embodiments of the inventive concept, the 3D polymer nanofiber membrane composed of 1D individual polymer nanofibers which are quasi-aligned and cross-laminated like grid structure with functions of controlling pore distribution and size may have an area ranged from 1 cm$^2$ to 1 m$^2$.

In embodiments of the inventive concept, an electrospinning pattern forming apparatus capable of manufacturing the 3D polymer nanofiber membrane composed of 1D individual polymer nanofibers which are quasi-aligned and cross-laminated like grid structure with functions of controlling pore distribution and size may include a high voltage generator, a rotatable conductive current collector, and a polymer solution injection nozzle connected to a metering pump, and double insulating blocks.

With this configuration, after placing the conductive current collector on a conductive substrate which is grounded, the grounded conductive substrate may be used as a cathode and the metering pump controllable in a discharging amount per time may be used as an anode. Then, the 3D polymer nanofiber membrane composed of the 1D individual polymer nanofibers which are quasi-aligned and cross-laminated like grid structure with functions of controlling pore distribution and size may be manufactured by applying a voltage of 5 to 20 kV and regulating a solution discharge rate in 5 to 200 μl/minute.

The double insulating blocks may be formed of a material which has a relative permittivity equal to or lower than 50. For example, the double insulating blocks may be made of one or more materials selected from a group of a Styrofoam material, a Teflon material, a wooden material, a plastic material, a glass material, a quartz material, a silicon oxide material, and a metallic material.

The double insulating blocks of the electrospinning pattern forming apparatus may be made of one or a mixture with one or more among a Styrofoam material, a Teflon material, a wooden material, a plastic material, a glass material, a quartz material, a silicon oxide material, and a metallic material. Nanofibers may be aligned in a direction and discharged through the electrospinning pattern forming apparatus employing the double insulating blocks which has permittivity equal to or lower than 50, and a grid structured membrane may be formed by a regular rotation of the conductive current collector which is rotatable in 90°.

The double insulating blocks of the electrospinning pattern forming apparatus may have widths and lengths ranged from 3 to 8 cm and heights ranged from 2 to 5 cm, and the two parallel insulating blocks may have an interval ranged from 1 to 6 cm. In the case that an interval between the double insulating blocks is shorter than 1 cm, the double insulating blocks may disturb alignment of the nanofibers. In the case that an interval between the double insulating blocks is longer than 6 cm, a degree of alignment of the nanofibers may be degraded because an electric field fails to be confined in a specific direction. An interval between top surfaces of the double insulating blocks and a tip of the nozzle may be ranged from 2 to 5 cm. An interval between bottom surfaces of the double insulating blocks and the conductive current collector may be ranged in 2 to 5 cm.

In this configuration, the double insulating blocks may change an electric field and may apply the electric field to the nanofibers in a specific direction to arrange the nanofibers.

Since a force is applied along two parallel insulating blocks, nanofibers may be arranged in a direction parallel to the two insulating blocks. If the nanofibers rotate with 90° after being arranged, the next nanofibers formed thereafter may be cross-laminated to the pre-arranged nanofibers. Repeated regular rotation may allow a 1D nanofibers cross-laminated and grid structured 3D nanofiber membrane to be formed.

Embodiments of the inventive concept provides a 3D polymer nanofiber membrane which, solving ununiformed pore sizes distribution that is concerned as the aforementioned problem arising from a polymer nanofiber membrane formed through a general electrospinning process, is controllable in porosity and pore sizes by parallelizing or crossing 1D nanofibers with 90°, and quasi-aligning and laminating the 1D nanofibers in a grid structure, and a manufacturing method thereof.

For this arrangement, an electrospinning pattern forming apparatus, including a high voltage generator, a rotatable conductive current collector, a polymer solution injection nozzle connected to a metering pump, and double insulating blocks, may be used to provide a 3D polymer nanofiber membrane composed of crossed or paralleled 1D polymer nanofibers, which are laminated, includes a quasi-aligned 3 D network structure, and a manufacturing method thereof.

In detail, embodiments of the inventive concept are directed to provide, first, a 3D polymer nanofiber membrane composed of crossed or paralleled 1D polymer nanofibers, which are laminated, includes a quasi-aligned 3 D network structure.

Second, embodiments of the inventive concept are directed to provide a 3D polymer nanofiber membrane having a uniform pore size and distribution by using a 3D polymer nanofibers network in which 1D polymer nanofibers manufactured through an electrospinning process are parallelized or cross-laminated and quasi-aligned in a grid structure.

A 3D polymer nanofiber membrane composed of crossed or paralleled 1D polymer nanofibers, which are laminated, includes a quasi-aligned 3 D network structure obtained from embodiments of the inventive concept may provide a uniform pore size and distribution by controlling diameters and intervals of 1D nanofibers.

An 1D polymer nanofibers may made of one, or a mixture with one or more among polyurethane, polyurethane copolymer, cellulose acetate, cellulose, acetate butyrate, cellulose derivative, styrene-acrylonitrile (SAN), polyacrylonitrile (PAN), poly(vinyl acetate) (PVAc), polyvinylpyrrolidone (PVP), polyvinyl alcohol (PVA), polyethylene oxide (PEO), polyacrylic acid (PAA), hydroxypropyl cellulose (HPC), polymethylmethacrylate (PMMA), polyfurfuryl alcohol (PFA), polystyrene (PS), polystyrene copolymer, polyaniline (PANT), polyvinylchloride (PVC), poly(vinylidene fluoride) (PVDF), polyethylene terephthalate (PET), polypropylene (PP) or polyethylene (PE), and polyimide.

It should be understood that the 1D individual polymer nanofibers obtained from embodiments of the inventive concept may have diameters ranged from 50 nm to 5 μm. It may be preferred to select the diameters from the range from 100 nm to 1 μm. In the case that diameters of the 1D individual nanofibers are smaller than 100 nm, a separation effect may be degraded due to an excessive increase of the porosity of the nanofiber membrane. In the case that diameters of the 1D individual nanofibers are higher than 1 μm, a separation effect may be also degraded due to a remarkable decrease of the porosity of the nanofiber membrane.

In embodiments of the inventive concept, the 3D polymer nanofiber membrane composed of crossed or paralleled 1D polymer nanofibers, which are laminated, includes a quasi-aligned 3D network structure, in which 1D individual nanofibers quasi-aligned, may have a thickness ranged from 10 to 200 μm. It may be more preferred to select a thickness of the 3D polymer nanofiber membrane from the range from 20 to 100 μm. In the case that a thickness of the 3D polymer nanofiber membrane is smaller than 20 μm, it would be concerned of degradation in mechanical strength. In the case that a thickness of the 3D polymer nanofiber membrane is larger than 100 μm, a degree of alignment of the nanofibers may be abruptly lower.

In embodiments of the inventive concept, the 3D polymer nanofiber membrane composed of crossed or paralleled 1D polymer nanofibers, which are laminated, includes a quasi-aligned 3D network structure, in which the 1D individual nanofibers quasi-aligned, may have nanofibers with their members at least equal to or more than 80% that are parallel or aligned in angles, which are equal to or smaller than 10°, to their adjacent polymer nanofibers.

In embodiments of the inventive concept, the 3D polymer nanofiber membrane composed of crossed or paralleled 1D polymer nanofibers, which are laminated, includes a quasi-aligned 3 D network structure 100, in which the 1D individual nanofibers are quasi-aligned, may include pores having an average diameter ranged from 10 nm to 10 μm. It may be more preferred for the 3D polymer nanofiber membrane to include pores having an average diameter of 50 nm to 1 μm. In the case that diameters of the pores are smaller than 50 nm, the separation efficiency may be degraded due to a remarkable decrease of the porosity of the nanofiber membrane. In the case that diameters of the pores are equal to or larger than 1 μm, the separation efficiency may be also degraded due to an excessive increase of porosity.

In embodiments of the inventive concept, the 3D polymer nanofiber membrane composed of crossed or paralleled 1D polymer nanofibers, which are laminated, includes a quasi-aligned 3 D network structure, in which the 1D individual nanofibers are quasi-aligned, may have porosity ranged from 50 to 90%. In the case that porosity is equal to or higher than 90%, such excessive porosity may degrade a separation effect. In the case that porosity is equal to or lower than 50%, transmittance thereof may be degraded.

FIG. 1 is a schematic diagram illustrating a 3D polymer nanofiber membrane manufactured through a general electrospinning method according a comparison example.

FIG. 1 shows a schematic pattern of the 3D polymer nanofiber membrane 100 manufactured through a general electrospinning method, in which the 1D individual nanofibers 110 are distributed at random. As such, the 3D polymer nanofiber membrane 100 according to the comparison example shows very different sizes of pore distribution, having a structure which is difficult in controlling pore sizes and distribution.

Figure 2:
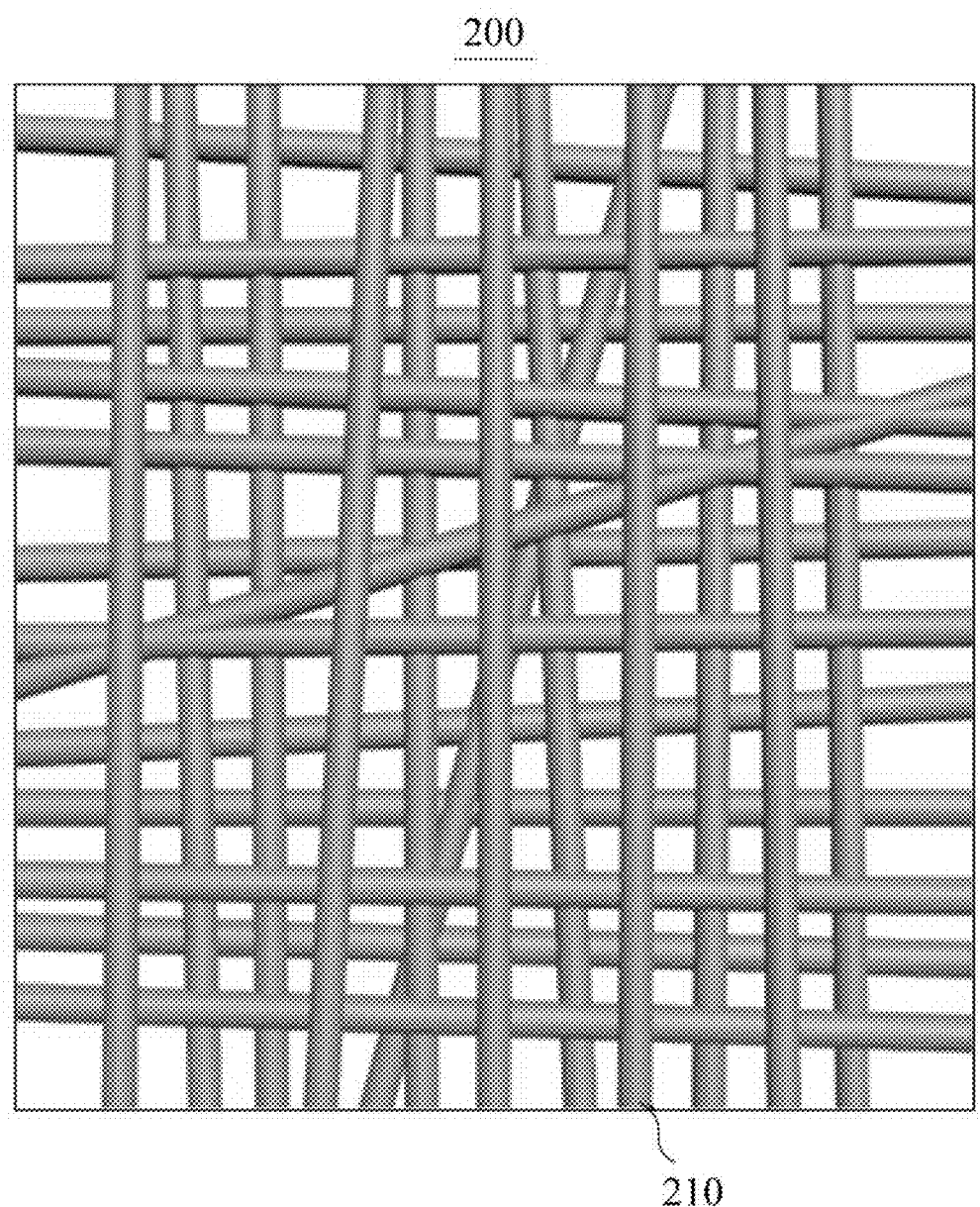
FIG. 2 is a schematic diagram illustrating a quasi-aligned 3D polymer nanofiber membrane according to an embodiment of the inventive concept.

FIG. 2 is a schematic diagram illustrating a quasi-aligned 3D polymer nanofiber membrane according to an embodiment of the inventive concept.

FIG. 2 shows a schematic pattern of a grid structure quasi-aligned 3D polymer nanofiber membrane 200 manufactured according to an embodiment of the inventive concept, in which 1D individual polymer nanofibers 210 are quasi-aligned in a grid structure. Different from the 3D polymer nanofiber membrane 100 according to the comparison example of FIG. 1, the 3D polymer nanofiber membrane 200 according to this embodiment has relatively uniform pore distribution and sizes. In other words, it can be seen that the 3D polymer nanofiber membrane 200 may be controlled in pore distribution and sizes as desired.

Figure 3:
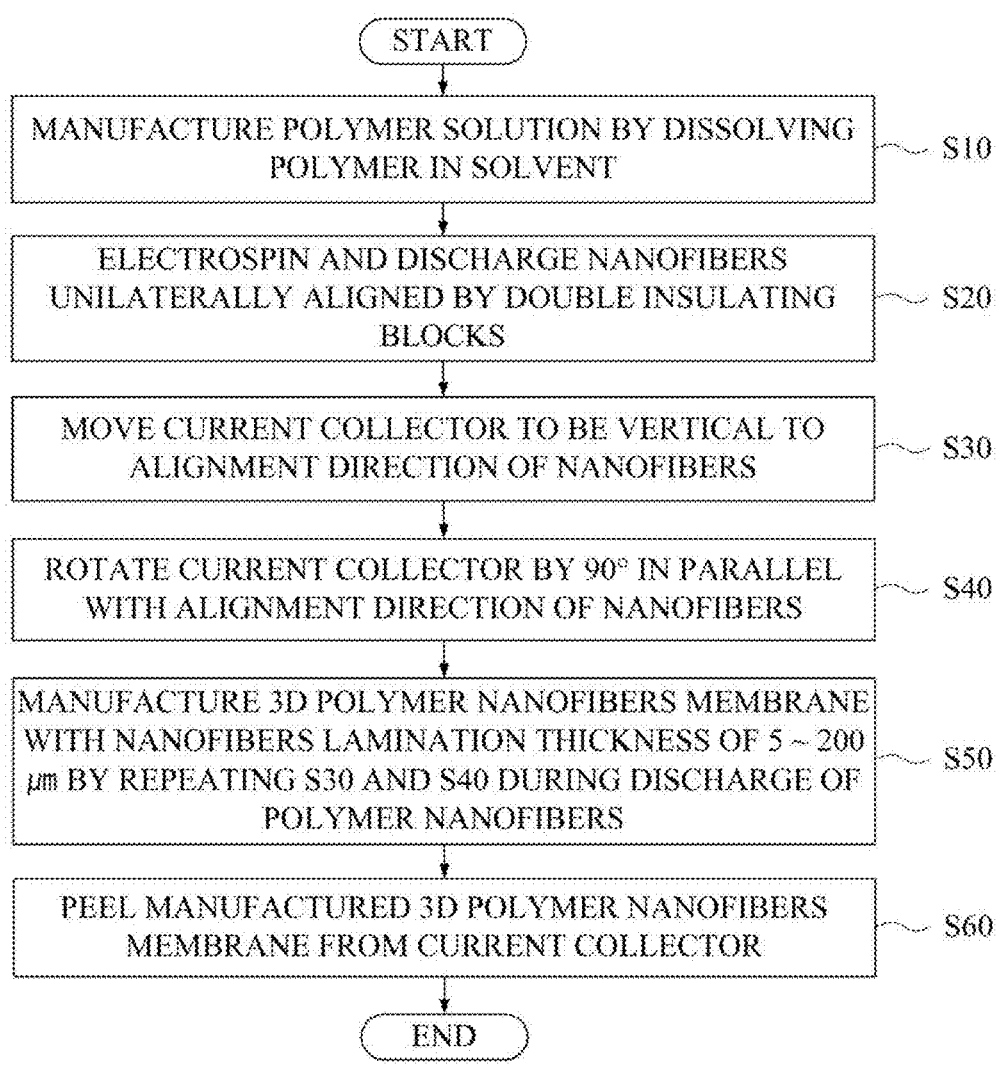
FIG. 3 is a flow chart showing a manufacturing method of a quasi-aligned 3D polymer nanofiber membrane according to an embodiment of the inventive concept.
Figure 4:
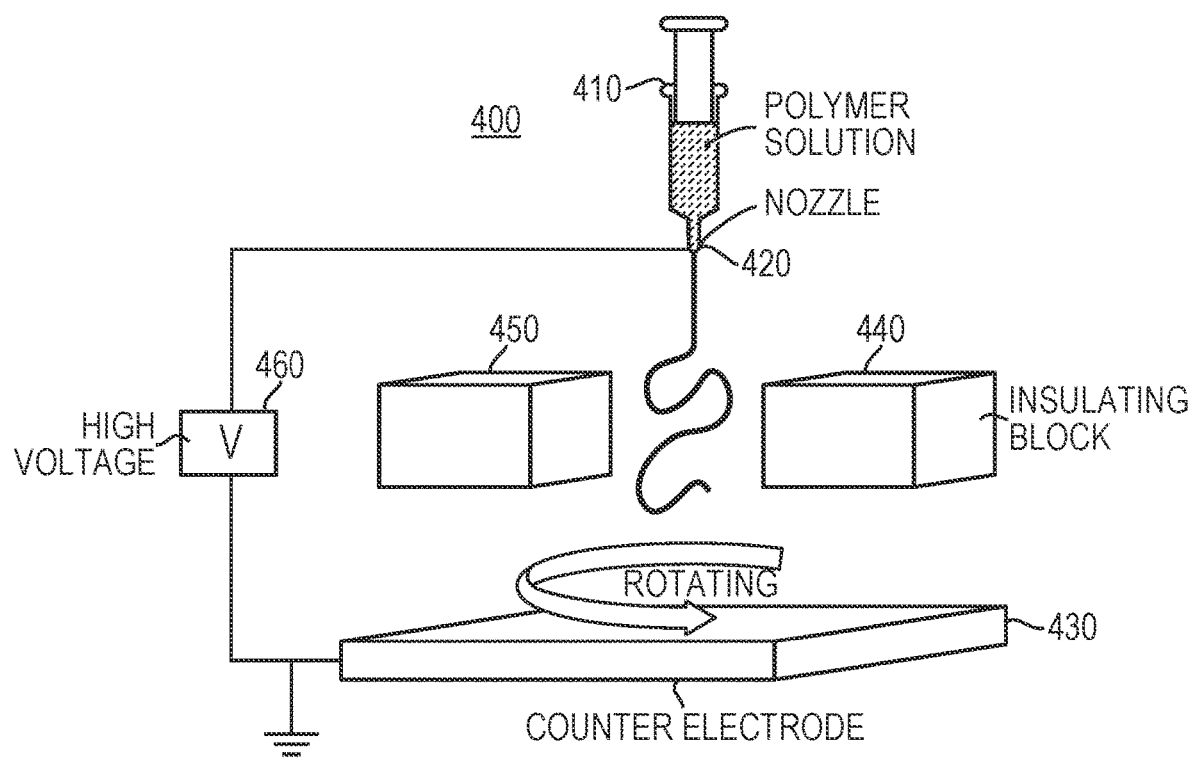
FIG. 4 is a diagram illustrating an electrospinning pattern forming apparatus according to an embodiment of the inventive concept.

FIG. 3 is a flow chart showing a manufacturing method of a grid structure cross-laminated, and pore distribution and size controlled 3D polymer nanofiber membrane according to an embodiment of the inventive concept, and FIG. 4 is a diagram illustrating an electrospinning pattern forming apparatus according to an embodiment of the inventive concept.

With reference to FIG. 3, a method of manufacturing a grid structure cross-laminated, and pore distribution and size controlled 3D polymer nanofiber membrane 200, in which the 1D individual nanofibers 210 are quasi-aligned, will be described in detail.

In this embodiment, a manufacturing method of a 3D polymer nanofiber membrane, which has 1D polymer nanofibers quasi-aligned in a grid structure, may be accomplished through the operations of: manufacturing a polymer solution by dissolving a polymer in a solvent (S10); electrospinning polymer nanofibers that are aligned in a direction by the double insulating blocks (S20); moving a current collector to be vertical to an alignment direction of the polymer nanofibers (S30); rotating the current collector as much as 90° in a direction parallel to the alignment direction of the polymer nanofibers (S40); manufacturing the 3D polymer nanofiber membrane in thicknesses of nanofibers from 5 to 200 µm by repeating the operations S30 and S40 while the polymer nanofibers are being discharged (S50); and peeling the manufactured 3D polymer nanofiber membrane from the current collector (S60).

In a process of manufacturing a 3D polymer nanofiber membrane, an electrospinning pattern forming apparatus, including a high voltage generator, a rotatable conductive current collector, a polymer solution injection nozzle connected to a metering pump, and double insulating blocks, may be used to manufacture the 3D polymer nanofiber membrane of a grid structure.

As such, according to embodiments of the inventive concept, it may be allowable to provide a grid structured 3D nanofiber membrane, which is controllable in pore sizes and distribution, by (1) adjusting diameters and intervals of the nanofibers and (2) parallelizing or cross-laminating the nanofibers.

The processing operations will be hereafter described in more detail.

First, in the operation S10, a polymer solution may be manufactured by dissolving a polymer in a solvent.

During this, the polymer may be made of one, or a mixture with one or more among polyurethane, polyurethane copolymer, cellulose acetate, cellulose, acetate butyrate, cellulose derivative, styrene-acrylonitrile (SAN), polyacrylonitrile (PAN), poly(vinyl acetate) (PVAc), polyvinylpyrrolidone (PVP), polyvinyl alcohol (PVA), polyethylene oxide (PEO), polyacrylic acid (PAA), hydroxypropyl cellulose (HPC), polymethylmethacrylate (PMMA), polyfurfuryl alcohol (PFA), polystyrene (PS), polystyrene copolymer, polyaniline (PANT), polyvinylchloride (PVC), poly(vinylidene fluoride) (PVDF), polyethylene terephthalate (PET), polypropylene (PP) or polyethylene (PE), and polyimide.

During this, the solvent may be any one, or a mixture with solvents different in boiling points, among water, N,N-dimethylformamide (DMF), N,N-dimethylacetamide (DMAc), N, methylpyrrolidon (NMP), ethanol ($CH_3CH_2OH$), methanol ($CH_3OH$), propanol ($C_3H_7OH$), tetrahydrofuran (THF), chloroform ($CHCl_3$), and acetone ($CH_3COCH_3$), and may be selected from solvents which can dissolve the polymer.

The polymer solution may contain a polymer of 5 to 15 weight % relative to a solvent.

In the operation S20, the polymer nanofibers may be aligned in a one-sided direction by transforming an electric field through the double insulating blocks and then applying the electrostatic force of the electric field in a specific direction to the nanofibers which are discharged.

For example, referring to FIG. 4, aligned polymer nanofibers may be manufactured by an electrospinning pattern forming apparatus 400. The electrospinning pattern forming apparatus 400 may place a rotatable conductive current collector 430 on a grounded conductive substrate. During this, the grounded conductive substrate may be used as a cathode, and an injection nozzle 420 attached to a metering pump 410, which is controlled in a discharge amount per time, may be used as an anode. A high voltage generator 460 may be selected in a voltage range from 1 to 30 kV. It may be preferred to adjust and apply a voltage in a range of 5~20 kV. The metering pump 410 may control a solution discharge rate in a range of 5~200 µl/minute.

During this, the double insulating blocks 440 and 450 of the electrospinning pattern forming apparatus 400, for example, insulating block 1 and insulating block 2, may control diameters of the nanofibers by transforming an electric field formed between the injection nozzle 420, which is connected to the metering pump 410, and the rotatable conductive current collector 430. In the case of strengthening the intensity of the electric field, the diameters of the nanofibers become smaller. If the intensity of the electric field is weaker, the diameters of the nanofibers become larger.

Additionally, the diameters of the nanofibers may be controlled by changing a solution discharge rate of the metering pump 410 of the electrospinning pattern forming apparatus 400. In the case with a higher solution discharge rate, the diameters of the nanofibers become larger. In the case with a lower solution discharge rate, the diameters of the nanofibers become smaller. Because a solution discharge rate lower than 5 µl/minute causes cutoff of the nanofibers and a solution discharge rate higher than 200 µl/minute causes generation of polymer drops, the solution discharge rate may be controlled in the range of 5~200 µl/minute as aforementioned.

Additionally, the 1D individual nanofibers may be aligned in a one-sided direction through the double insulating blocks 440 and 450 respectively of insulating block 1 and insulating block 2. During this, it should be understood that diameters of the 1D individual nanofibers are ranged from 50 nm to 2 µm. It may be more preferred to select the diameters of the 1D individual nanofibers in a range of 100~500 nm. In the case that the diameters of the 1D individual nanofibers are smaller than 100 nm, the porosity of the nanofiber membrane may become excessively higher to degrade a separation effect. In the case that the diameters of the 1D individual nanofibers are larger than 500 nm, the porosity of the nanofiber membrane may become remarkably lower to also degrade a separation effect.

During this, it may be permissible to control intervals and sizes of pores of the 3D nanofiber membrane by adjusting diameters of the nanofibers. The intensity of the electric field between the injection nozzle 420 and the rotatable conductive current collector 430 may be settled by (1) a voltage applied to the injection nozzle 420, and (2) an interval between the injection nozzle 420 and the rotatable conductive current collector 430.

Additionally, the double insulating blocks 440 and 450 of insulating block 1 and insulating block 2 may respectively have widths and lengths ranged from 3 to 8 cm and heights ranged from 2 to 5 cm, and the two parallel insulating blocks may have an interval (a distance between insulating block 1 440 and insulating block 2 450) ranged from 1 to 6 cm. In the case that an interval between the double insulating blocks is shorter than 1 cm, the double insulating blocks may disturb alignment of the nanofibers. Additionally, in the case that an interval between the double insulating blocks is longer than 6 cm, a degree of alignment of the nanofibers may be degraded because an electric field fails to be confined in a specific direction. An interval between top surfaces of the double insulating blocks and a tip of the nozzle may be ranged from 2 to 5 cm. An interval between bottom surfaces of the double insulating blocks and the conductive current collector 430 may be ranged in 2 to 5 cm.

The double insulating blocks may be made of a material having a relative permittivity equal to or lower than 50. For example, the double insulating blocks may be made of one or more selected from a group of among a Styrofoam material, a Teflon material, a wooden material, a plastic material, a glass material, a quartz material, a silicon oxide material, and a metallic material.

Returning to FIG. 3, in the operation S30, the 1D polymer nanofibers may be manufactured to locate in parallel with a uniform interval by moving the conductive current collector to be vertical to the alignment direction of the nanofibers.

For example, nanofibers discharged through the injection nozzle 420 may be aligned in a one-sided direction and accommodated in the conductive current collector 430 through the double insulating blocks. During this, the conductive current collector 430 may move to be vertical to the alignment direction of the nanofibers. A moving speed of the conductive current collector 430 may be controlled in the range from 1 mm/s to 50 mm/s, and a moving interval of the conductive current collector 430 may be controlled in the range from 1 cm to 20 cm.

During this, an interval between most adjacent polymer nanofibers in the 3D polymer nanofiber membrane may be controlled in the range from 5 nm to 20 μm.

Referring again to FIG. 3, in the operation S40, a polymer nanofibers grid, in which polymer nanofibers are crossed each other, may be formed by rotating the conductive current collector by 90° in a direction parallel to the alignment direction of the nanofibers.

For example, the double insulating blocks 440 and 450 respectively of insulating block 1 and insulating block 2 may align the nanofibers by transforming an electric field and applying the transformed electric field to the nanofibers in a specific direction. The nanofibers may be aligned in a direction parallel to the double insulating blocks by applying a force along the double insulating blocks which are disposed in parallel. If the conductive current collector 430 is rotated by 90° in the direction parallel to the alignment direction of the nanofibers after arranging the nanofibers, the next nanofibers formed later may be laminated cross to the previously arranged nanofibers.

Repetitive and regular move and rotation of the conductive current collector 430 may allow a 1D nanofibers cross-laminated and grid structured 3D nanofiber membrane. For this formation, the operation S50 of FIG. 3 may proceed to manufacture a 3D polymer nanofibers network, in which polymer nanofibers are laminated in a grid structure, by repeating the operations S30 and S40 described above.

During this, the 3D polymer nanofiber membrane composed of 1D individual polymer nanofibers which are quasi-aligned and cross-laminated like grid structure with functions of controlling pore distribution and size may include pores having an average diameter ranged from 10 nm to 10 μm. It may be more preferred for the 3D polymer nanofiber membrane to include pores having an average diameter of 50 nm to 1 μm. In the case that diameters of the pores are smaller than 50 nm, the separation efficiency may be degraded due to a remarkable decrease of the porosity of the nanofiber membrane. In the case that diameters of the pores are equal to or larger than 1 μm, the separation efficiency may be also degraded due to an excessive increase of porosity.

In embodiments of the inventive concept, the 3D polymer nanofiber membrane composed of 1D individual polymer nanofibers which are quasi-aligned and cross-laminated like grid structure with functions of controlling pore distribution and size may have porosity ranged from 50 to 90%. In the case that porosity is equal to or higher than 90%, such excessive porosity may degrade a separation effect. In the case that porosity is equal to or lower than 50%, transmittance thereof may be degraded.

As another embodiment, the electrospinning pattern forming apparatus 400 described in conjunction with FIG. 4 may be implemented in a multi-nozzle system formed of 10,000 or more needles or may be also allowable in mass production using a cylindrical drum.

Returning to FIG. 3, in the operation S60, a grid structure quasi-aligned and laminated 3D polymer nanofiber membrane may be manufactured by peeling the 3D polymer nanofibers network, which is manufactured on the conductive current collector, from the conductive current collector.

During this, the 3D polymer nanofiber membrane composed of 1D individual polymer nanofibers which are quasi-aligned and cross-laminated like grid structure with functions of controlling pore distribution and size may have an area ranged from 1 cm$^2$ to 1 m$^2$.

As such, the nanofibers quasi-aligned, grid structure cross-laminated, and pore distribution and size controlled 3D polymer nanofiber membrane may be formed by controlling intervals and angles between the nanofibers which are discharged from the injection nozzle through move and rotation of the conductive current collector.

According to embodiments of the inventive concept, for the purpose of allowing the 3D polymer nanofiber membrane to have at least one of functionalities of hydrophilicity, hydrophobicity, oxidation resistivity, thermal resistivity, and chemical resistivity, the manufacturing method of FIG. 3 may further include the operation (not shown) of coating the surface of the 3D polymer nanofiber membrane with at least one of a polymer, a ceramic material, a metal, and a metal oxide.

Figure 5:
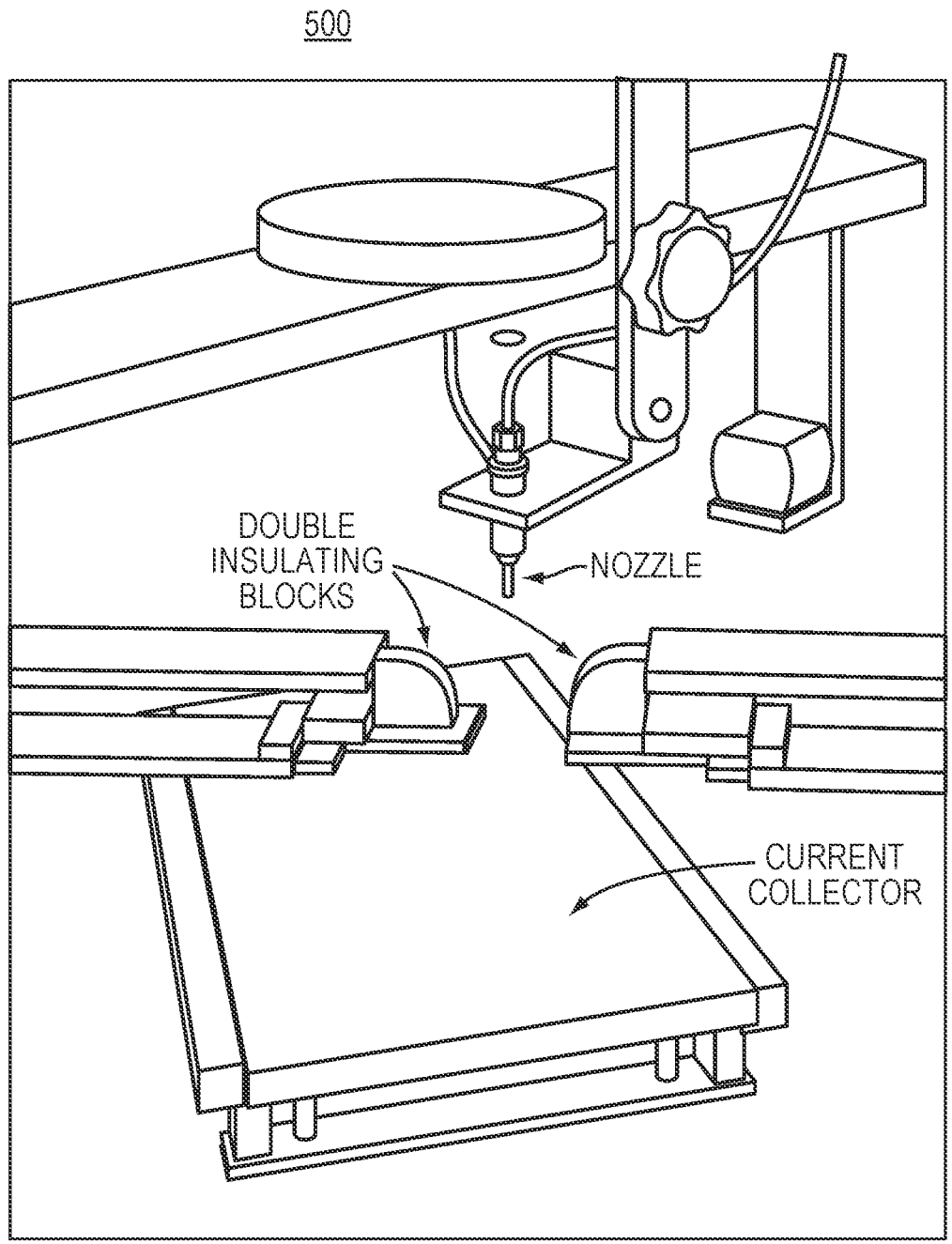
FIG. 5 shows a practical photograph of an electrospinning pattern forming apparatus according to an embodiment of the inventive concept.

FIG. 5 shows a practical photograph of an electrospinning pattern forming apparatus according to an embodiment of the inventive concept. The photograph 500 of FIG. 5 is a photographic example of a practical pattern forming apparatus corresponding to the electrospinning pattern forming apparatus 400 described in conjunction with FIG. 4. The photograph 500 shows a nozzle for injecting a polymer solution, double insulating blocks, and a current collector.

Now practical embodiments and comparison examples will be introduced to describe the inventive concept. However, these embodiments and comparison examples should not be regarded as restricting the inventive concept.

Embodiment 1

3D Polymer (PEO) Nanofiber Membrane where 1D Individual Nanofibers are Quasi-Aligned by Electrospinning Pattern Forming Apparatus A manufacturing method of a 3D polymer (PEO) nanofiber membrane, in which 1D individual nanofibers are quasi-aligned by an electrospinning pattern forming apparatus, will be described in detail hereafter by operations according to Embodiment 1.

(a) The operation of dissolving a polymer (PEO) in a solvent (DMF) which has solubility to the polymer and electrospinning polymer nanofibers which are aligned in a one-sided direction by an electrospinning pattern forming apparatus including double insulating blocks.

First, after putting PEO of 1 g into DMF of 9 g, the polymer solution of PEO and DMF was agitated at 30° C. for 5 hours. After pouring the agitated polymer solution into a metering pump, 1D nanofibers unilaterally aligned by parallel double insulating blocks were obtained by applying a high voltage to an injection nozzle connected to the metering pump and by electrospinning the polymer solution. The electrospinning was carried out by applying a voltage of 10 kV and a size of the injection nozzle was 23 GA. An interval of the current collector and the injection nozzle was 10 cm and the electrospinning was carried out with a discharge rate of 200 µl/minute. The double insulating blocks used glass blocks each of which has a height of 5 cm and a width of 2 cm. An interval between the parallel double insulating blocks was 5 cm, an interval between the tops of the insulating blocks and the injection nozzle was 2 cm, and an interval between the bottoms of the double insulating blocks and the current collector was 5 cm. A substrate of the current collector was fabricated and used a stainless steel substrate in a size of 10 cm×10 cm. The current collector moved with 5 mm/second in an interval of 10 cm to be vertical to an alignment direction of the nanofibers.

(b) The operation of rotating the conductive current collector by 90° in a direction parallel to the alignment direction of the unilaterally aligned polymer (PEO) nanofibers in the electrospinning pattern forming apparatus.

After moving the conductive current collector to be vertical to the alignment direction of the obtained aligned polymer (PEO) nanofibers, the conductive current collector was rotated by 90°. Then, the nanofibers were obtained in alignment cross to the previously arranged nanofibers.

(c) The operation of manufacturing a 3D polymer nanofiber membrane, by laminating the aligned polymer (PEO) nanofibers, and peeling the membrane from the current collector.

Embodiment 1 was carried out to form the aligned nanofibers through electrospinning discharge and move of the conductive current collector, and to manufacture the cross-aligned nanofibers through the 90° rotation of the conductive current collector. Additionally, those processes were repeated in 100 times to manufacture a 3D polymer (PEO) nanofiber membrane having a thickness of 50 µm. Then, a resultant 3D polymer (PEO) nanofiber membrane was formed by peeling the 3D polymer (PEO) nanofiber membrane, which was manufactured on the conductive current collector, from a stainless steel current collector substrate.

Embodiment 2

3D Polymer (PAN) Nanofiber Membrane where 1D Individual Nanofibers Are Quasi-Aligned by Electrospinning Pattern Forming Apparatus A manufacturing method of a 3D polymer (PAN) nanofiber membrane, in which 1D individual nanofibers are quasi-aligned by an electrospinning pattern forming apparatus, will be described in detail hereafter by operations according to Embodiment 2.

(a) The operation of dissolving a polymer (PAN) in a solvent (DMF) which has solubility to the polymer and electrospinning polymer nanofibers which are aligned in a one-sided direction by an electrospinning pattern forming apparatus including double insulating blocks.

First, after putting PAN of 1 g into DMF of 9 g, the polymer solution of PAN and DMF was agitated at 80° C. for 5 hours. After pouring the agitated polymer solution into a metering pump, 1D nanofibers unilaterally aligned by parallel double insulating blocks were obtained by applying a high voltage to an injection nozzle connected to the metering pump and by electrospinning the polymer solution. The electrospinning was carried out by applying a voltage of 10 kV and a size of the injection nozzle was 23 GA. An interval of the current collector and the injection nozzle was 10 cm and the electrospinning was carried out with a discharge rate of 200 µl/minute. The double insulating blocks used glass blocks each of which has a height of 5 cm and a width of 2 cm. An interval between the parallel double insulating blocks was 5 cm, an interval between the tops of the insulating blocks and the injection nozzle was 2 cm, and an interval between the bottoms of the double insulating blocks and the current collector was 5 cm. A substrate of the current collector was fabricated and used a stainless steel substrate in a size of 10 cm×10 cm. The current collector moved with 5 mm/second in an interval of 10 cm and then turned to be vertical to an alignment direction of the nanofibers.

(b) The operation of rotating the conductive current collector by 90° in a direction parallel to the alignment direction of the unilaterally aligned polymer (PAN) nanofibers in the electrospinning pattern forming apparatus.

After moving the conductive current collector to be vertical to the alignment direction of the obtained aligned polymer (PAN) nanofibers, the conductive current collector was rotated by 90°. Then, the nanofibers were obtained in alignment cross to the previously arranged nanofibers.

(c) The operation of manufacturing a 3D polymer nanofiber membrane, by laminating the aligned polymer (PAN) nanofibers, and peeling the membrane from the current collector.

Embodiment 2 was carried out to form the aligned nanofibers through electrospinning discharge and to manufacture the cross-aligned nanofibers through the 90° rotation of the conductive current collector. Additionally, those processes were repeated in 100 times to manufacture a 3D polymer (PAN) nanofiber membrane having a thickness of 50 µm. Then, a resultant 3D polymer (PAN) nanofiber membrane was formed by peeling the 3D polymer (PAN) nanofiber membrane, which was manufactured on the conductive current collector, from a stainless steel current collector substrate.

Comparison 1

3D Polymer (PAN) Nanofiber Membrane Manufactured Through Electrospinning

A manufacturing method of a 3D polymer (PAN) nanofiber membrane through an electrospinning process will be described in detail hereafter.

(a) The operation of dissolving a polymer (PAN) in a solvent (DMF) to prepare a polymer solution and electrospinning polymer nanofibers.

After putting PAN of 1 g into DMF of 9 g, the polymer solution of PAN and DMF was agitated at 80° C. for 5 hours. Polymer (PAN) nanofibers were obtained by performing an electrospinning with the agitated polymer solution. The electrospinning was carried out by applying a voltage of 15 kV and a size of an injection nozzle was 23 GA. An interval of a current collector and the injection nozzle was 15 cm and the electrospinning was carried out with a discharge rate of 200 μl/minute. A substrate of the current collector was fabricated and used in a size of 10 cm×10 cm. A polymer (PAN) nanofibers mat was manufactured through this method.

Figure 6A:
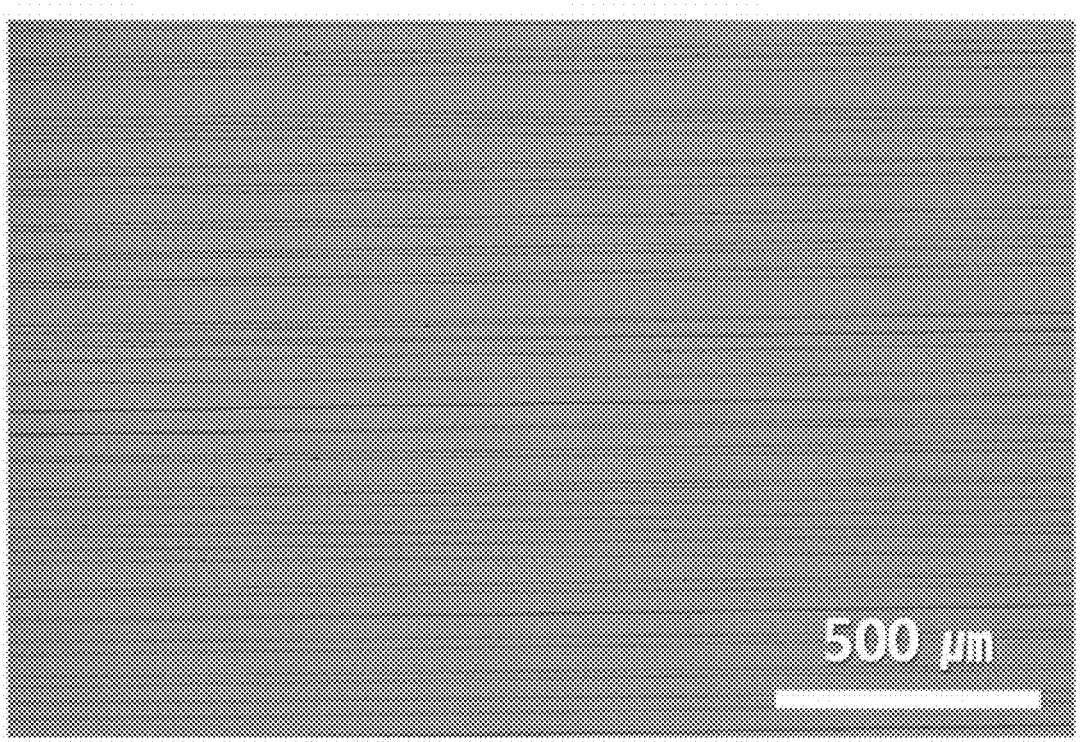
FIGS. 6A and 6B show optical microscopic photographs taken from a one-directional pattern of polyethylene oxide (PEO) nanofibers according to an embodiment of the inventive concept.
Figure 6B:
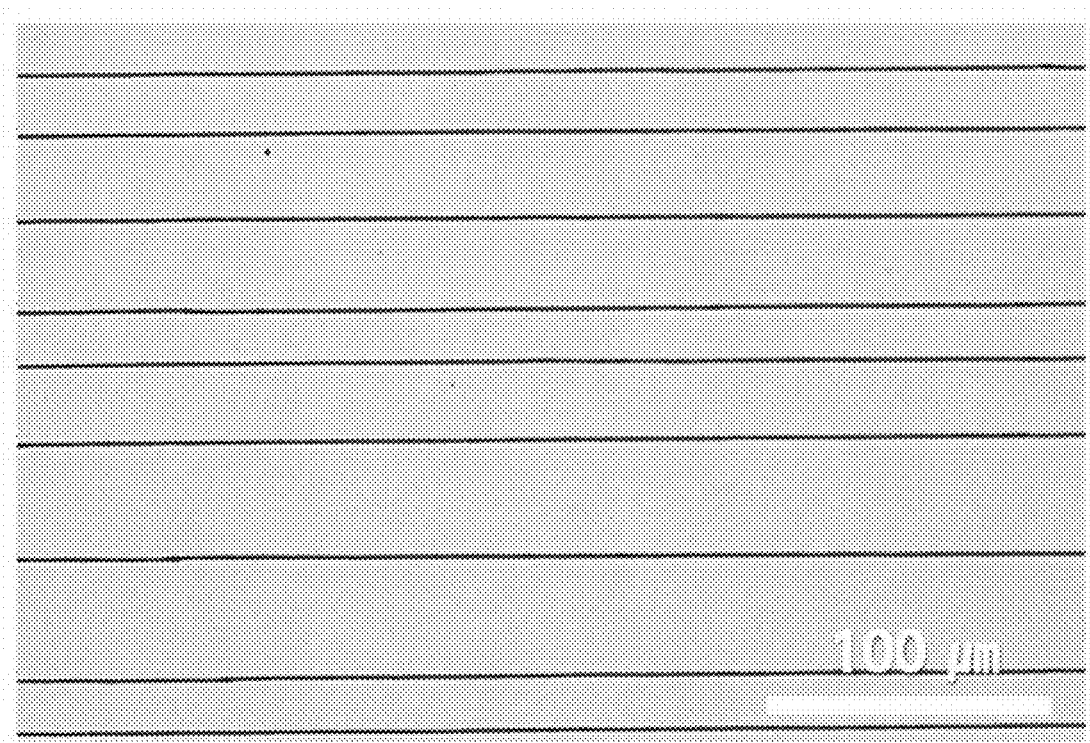

FIGS. 6A and 6B show optical microscopic photographs taken from a one-directional pattern of polyethylene oxide (PEO) nanofibers according to Embodiment 1.

As shown in FIG. 6A, the polyethylene oxide (PEO) nanofibers were formed in a direction in parallel each other.

Additionally, as shown in FIG. 6B, the polyethylene oxide (PEO) with a uniform thickness were formed, in a direction, in an interval ranged from 10 to 50 μm without disconnection.

Figure 7A:
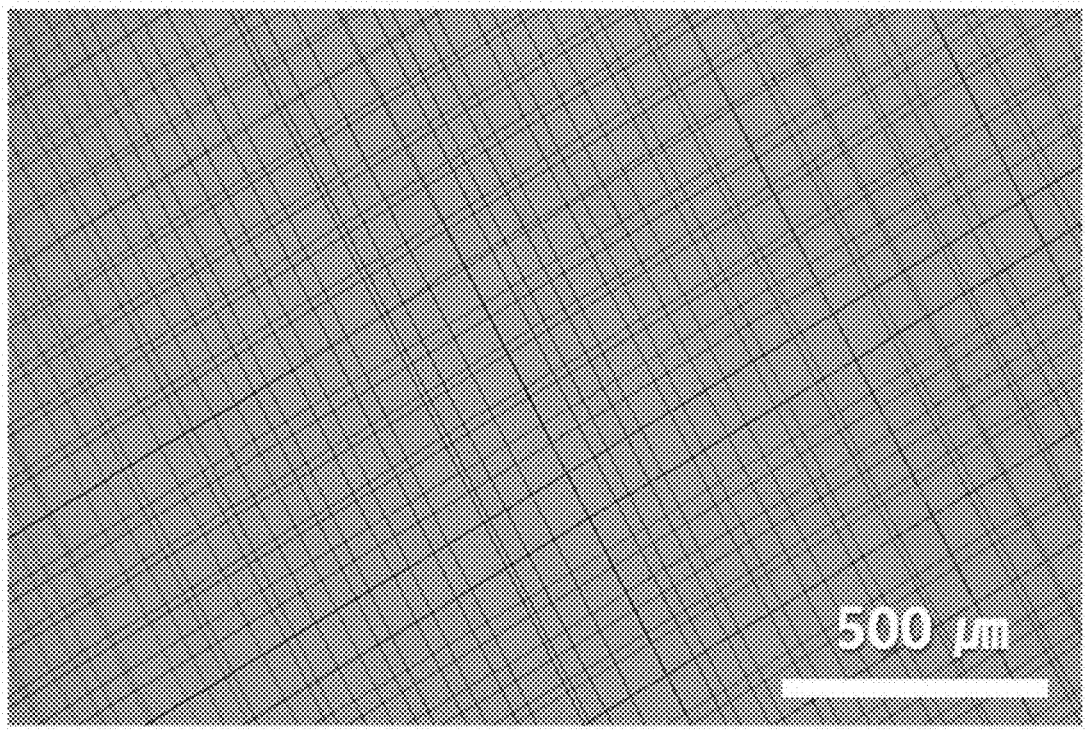
FIGS. 7A and 7B show optical microscopic photographs taken from a cross pattern of polyethylene oxide (PEO) nanofibers according to an embodiment of the inventive concept.
Figure 7B:
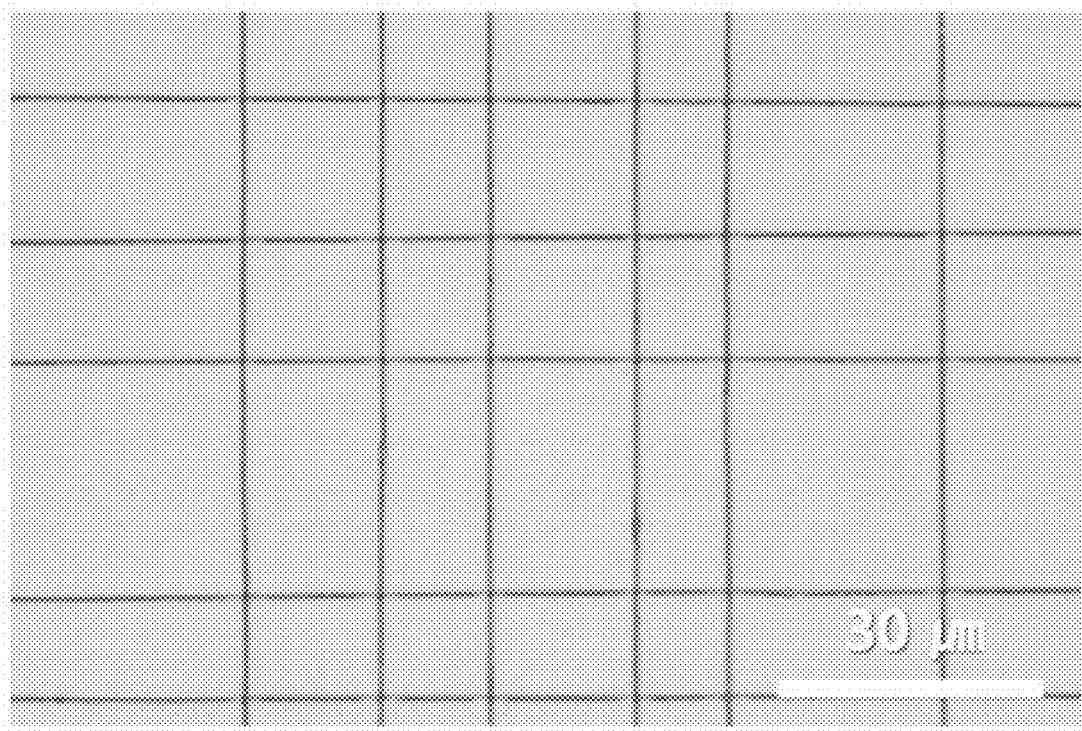

FIGS. 7A and 7B show optical microscopic photographs taken from a cross pattern of polyethylene oxide (PEO) nanofibers according to Embodiment 1.

From FIGS. 7A and 7B, it can be seen that the polyethylene oxide (PEO) nanofibers are formed in a cross pattern and diameters of pores defined by the cross of the nanofibers are ranged from 10 to 30 μm.

Figure 8A:
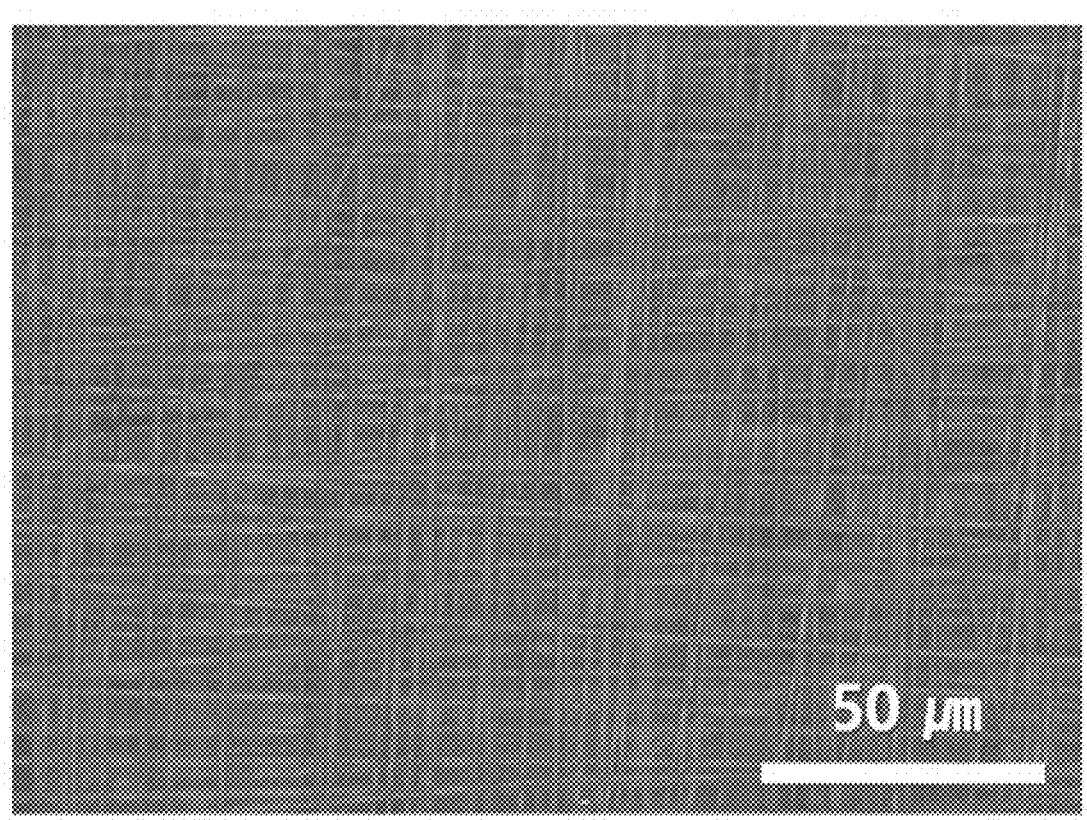
FIGS. 8A and 8B show optical microscopic photographs taken from a cross pattern of polyacrylonitrile (PAN) nanofibers according to an embodiment of the inventive concept.
Figure 8B:
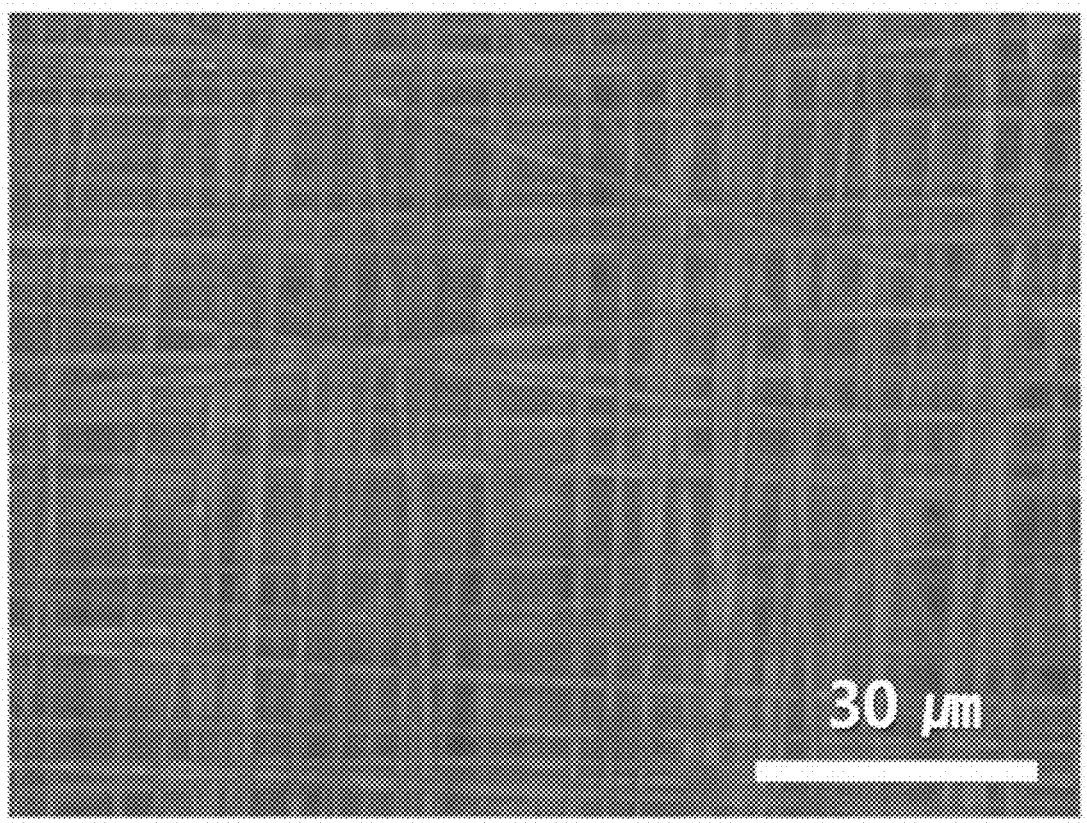

FIGS. 8A and 8B show optical microscopic photographs taken from a cross pattern of polyacrylonitrile (PAN) nanofibers according to Embodiment 2.

Referring to FIG. 8B, different from Comparison 1 that will be described later, Embodiment 2 has a quasi-aligned nanofibers network. Additionally, nanofibers equal to or larger than 80% thereabout are formed in a cross pattern between them and diameters of pores defined by the cross of the nanofibers are ranged from 1 to 10 μm.

Figure 9A:
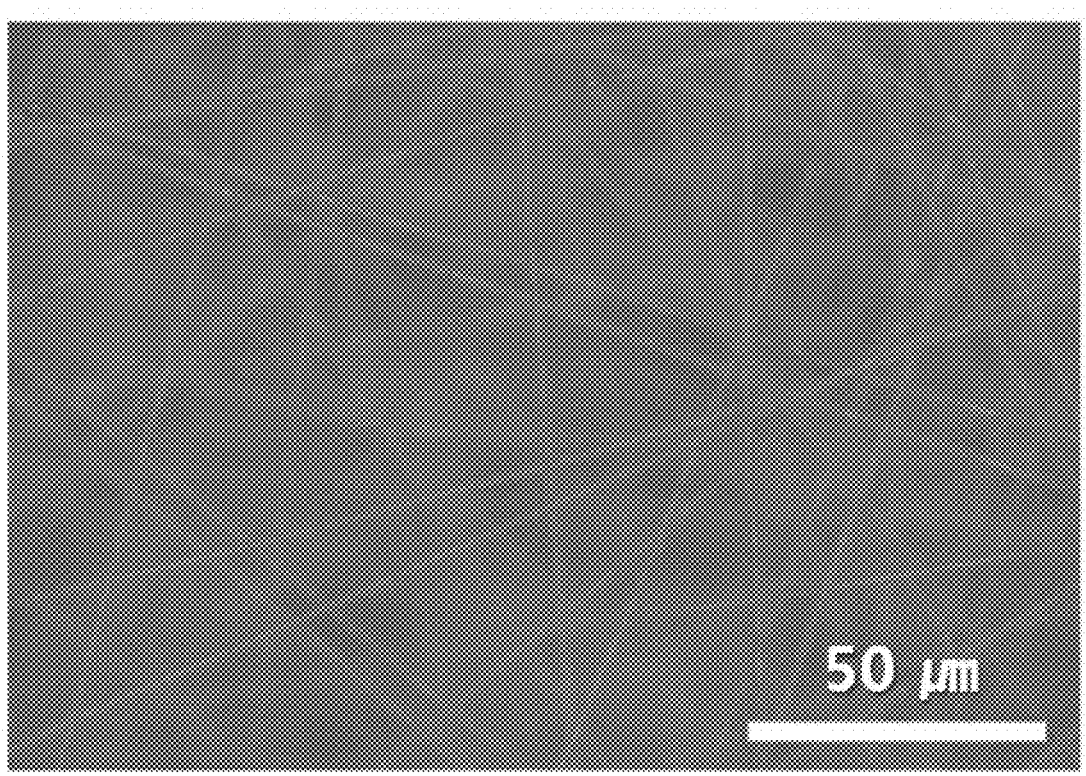
FIGS. 9A and 9B show optical microscopic and Scanning Electron Microscopic (SEM) photographs taken from polyacrylonitrile (PAN) nanofibers according to a comparison example of the inventive concept.
Figure 9B:
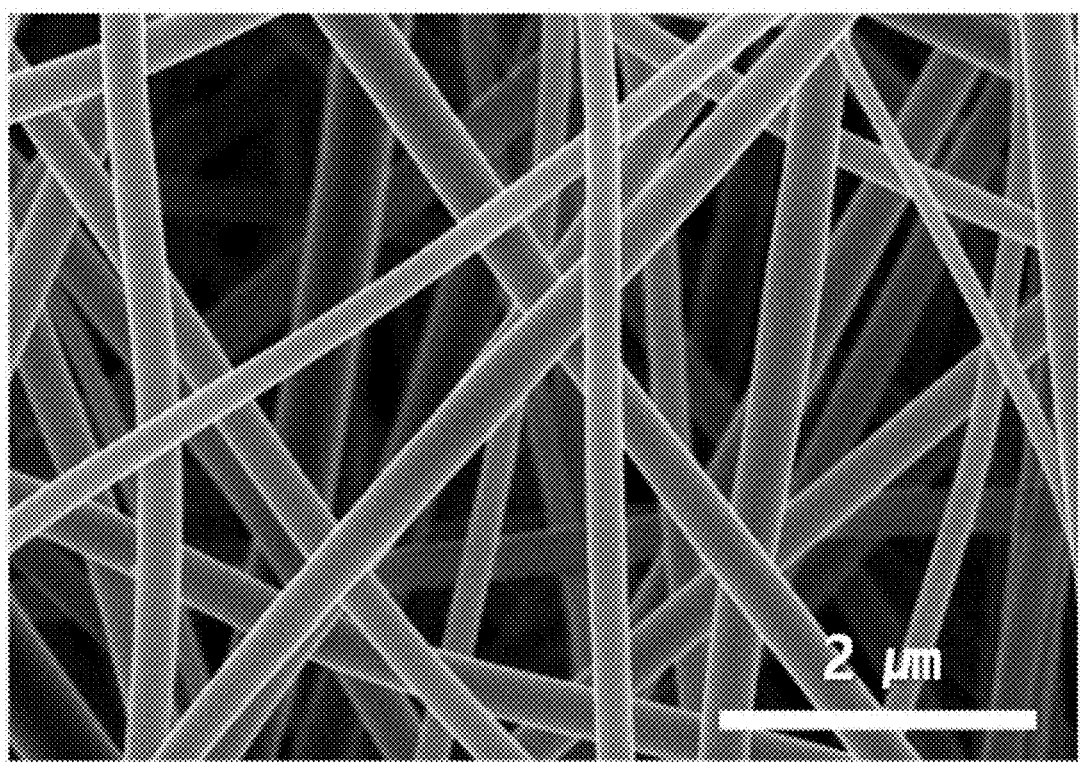

FIGS. 9A and 9B show optical microscopic and Scanning Electron Microscopic (SEM) photographs taken from polyacrylonitrile (PAN) nanofibers according to Comparison 1.

Referring to FIGS. 9A and 9B, it can be seen that the polyacrylonitrile (PAN) nanofiber membrane is formed as randomly directional nanofibers and diameters of pores between the nanofibers are very ununiform from several tens micrometers (μm) to several nanometers (nm).

As can be comparatively known from Embodiment 2 with Comparison 1, since the 3D nanofiber membrane manufactured through the electrospinning pattern forming apparatus is easier in controlling pore sizes than a nanofiber membrane manufactured a general electrospinning method, it may be allowable to uniformly control a pore distribution and thereby to secure air-permeability and separability of the nanofiber membrane.

In the case of manufacturing a 3D polymer nanofiber membrane through an electrospinning pattern forming apparatus, (1) it may be allowable to manufacture a 3D polymer nanofibers network in which 1D polymer nanofibers are parallelized or cross-laminated and quasi-aligned, and (2) it may be allowable to provide a uniform pore size and distribution controlled 3D polymer nanofiber membrane by using in which 1D individual polymer nanofibers which are quasi-aligned and cross-laminated like grid structure.

Especially, according to embodiments of the inventive concept, it may be accomplishable to have high economic feasibility because an one-directionally aligned 1D polymer nanofibers structure is manufactured by using an electrospinning pattern forming apparatus in which double insulating blocks are installed in parallel with an electrospinning direction.

According to embodiments of the inventive concept, the quasi-aligned, and pore size and distribution controller 3D polymer nanofiber membrane may be manufactured by using an electrospinning pattern forming apparatus that includes double insulating blocks forming quasi-aligned nanofibers through transformation of an electric field, and includes a current collector rotatable in 90°. Additionally, a 3D polymer nanofiber membrane manufactured according to embodiments of the inventive concept may be utilized for air filters, separation membranes, water qualification filters, cell culturing membranes, and so on by allowing various properties thereto through functional surface coating.

While embodiments of the present disclosure have been shown and described with reference to the accompanying drawings thereof, it will be understood by those skilled in the art that various changes and modifications in form and details may be made therein without departing from the spirit and scope of the present disclosure as defined by the appended claims and their equivalents. For example, it may be allowable to achieve desired results although the embodiments of the present disclosure are performed in other sequences different from the descriptions, and/or the elements, such as system, structure, device, circuit, and so on, are combined or assembled in other ways different from the descriptions, replaced or substituted with other elements or their equivalents.

Therefore, other implementations, other embodiments, and equivalents of the appended claims may be included in the scope of the appended claims.

What is claimed is:

1. A polymer nanofiber membrane comprising:
quasi-aligned and cross-laminated individual polymer nanofibers in a grid structure with controlled pore distribution and size, the grid structure having a first direction orthogonal to a second direction, a first portion of the individual polymer nanofibers being generally oriented in the first direction wherein 1) at least 80% of the first portion of the individual polymer nanofibers are oriented within 10° of the first direction, and 2) the first portion of individual polymer nanofibers includes individual polymer nanofibers that are not parallel to the first direction.

2. The polymer nanofiber membrane of claim 1, wherein the diameter of the individual polymer nanofibers is from 50 nm to 5 μm.

3. The polymer nanofiber membrane of claim 1, wherein the lamination thicknesses of the individual polymer nanofibers is from 5 to 200 μm.

4. The polymer nanofiber membrane of claim 1, a second portion of the individual polymer nanofibers being generally oriented in the second direction wherein 1) at least 80% of the second portion of the individual polymer nanofibers are oriented within 10° of the second direction, and 2) the second portion of individual polymer nanofibers including individual polymer nanofibers that are not parallel to the second direction.

5. The polymer nanofiber membrane of claim 1, wherein the pores have an average diameter from 10 nm to 10 μm.

6. The polymer nanofiber membrane of claim 1, wherein the porosity of the polymer nanofiber membrane is from 50 to 90%.

7. The polymer nanofiber membrane of claim 1, wherein the area of the polymer nanofiber membrane is from 1 cm$^2$ to 1 m$^2$.

8. The polymer nanofiber membrane of to claim 1 and forming at least one of an air filter, a separator, a water filter, and a cell culture filter.

9. A polymer nanofiber membrane comprising individual polymer nanofibers that are cross-laminated in a grid structure having a first direction orthogonal to a second direction, a first portion of the individual polymer nanofibers being generally oriented in the first direction wherein 1) at least 80% of the first portion of the individual polymer nanofibers are oriented within 10° of the first direction, and 2) the first portion of individual polymer nanofibers includes individual polymer nanofibers that are not parallel to the first direction, the polymer nanofiber membrane being manufactured by an electrospinning pattern forming apparatus comprising a high voltage generator, a conductive current collector, a polymer solution injection nozzle connected to a metering pump, and a plurality of insulating blocks.

10. The polymer nanofiber membrane of claim 9, wherein the high voltage generator is configured to apply a voltage between 1 kV and 30 kV, and
wherein the metering pump is configured to discharge a polymer solution at a rate between 5 µl/minute and 200 µl/minute.

11. The polymer nanofiber membrane of claim 9, wherein the plurality of insulating blocks comprise one or a mixture with two or more among a Styrofoam material, a Teflon material, a wooden material, a plastic material, a glass material, a quartz material, a silicon oxide material, and a metallic material, and has a relative permittivity equal to or lower than 50.

12. The polymer nanofiber membrane of claim 9, wherein the plurality of insulating blocks each have a width and a length from 3 to 8 cm and a height from 2 to 5 cm, and an interval between two of the plurality of insulating blocks has a distance from 1 to 6 cm.

13. The polymer nanofiber membrane of claim 9, wherein an interval between top surfaces of the plurality of insulating blocks and a tip of the injection nozzle is from 2 to 5 cm, and an interval between bottom surfaces of the double insulating blocks and the conductive current collector is ranged from 2 to 5 cm.

14. The polymer nanofiber membrane of claim 9, wherein, in the electrospinning pattern forming apparatus, the nanofibers are discharged and aligned in one direction by the plurality of insulating blocks, and a grid-structured membrane is formed by movement and rotation of the conductive current collector relative to the plurality of insulating blocks.

15. A polymer nanofiber membrane comprising individual polymer nanofibers that are cross-laminated in a grid structure, the grid structure having a first direction orthogonal to a second direction, wherein at least a portion of the individual polymer nanofibers are generally oriented in the first direction and are not parallel to the first direction, the polymer nanofiber membrane being prepared by a process comprising:
discharging and electrospinning the individual polymer nanofibers into a space adjacent to a plurality of insulating blocks;
collecting the discharged individual polymer nanofibers at a conductive current collector to form a first layer of the individual polymer nanofibers in the first direction; and
collecting the discharged individual polymer nanofibers at the conductive current collector to form a second layer of the individual polymer nanofibers in the second direction.

16. The polymer nanofiber membrane of claim 15, wherein at least 80% of the individual polymer nanofibers in the first direction are oriented within 10° of the first direction.

17. The polymer nanofiber membrane of claim 15, wherein the process by which the membrane is prepared further comprises rotating the conductive current collector relative to the plurality of insulating blocks prior to collecting the discharged polymer nanofibers at the conductive current collector to form the second layer.

18. The polymer nanofiber membrane of claim 15, wherein discharging and electrospinning the individual polymer nanofibers includes discharging a solution comprising a polymer, the solution being 5-15% polymer by weight.

19. The polymer nanofiber membrane of claim 15, wherein the polymer nanofiber membrane has a nanofiber lamination thickness between 5 and 200 µm.

20. The polymer nanofiber membrane of claim 15, wherein discharging and electrospinning the individual polymer nanofibers includes discharging a polymer solution through at least one injection nozzle connected to a terminal of a high voltage generator.

21. The polymer nanofiber membrane of claim 15, wherein the process further comprises, during collection of the discharged individual polymer nanofibers, controlling a moving speed of the conductive current collector at a speed between 1 mm/s and 50 mm/s and controlling a moving distance of the conductive current collector between 1 cm and 20 cm.

22. The polymer nanofiber membrane of claim 15, wherein the process further comprises coating a surface of the polymer nanofiber membrane with a layer of at least one of a polymer, a ceramic material, a metal, and a metal oxide, the layer providing at least one of hydrophilicity, hydrophobicity, oxidation resistivity, thermal resistivity, and chemical resistivity to the polymer nanofiber membrane.

* * * * *